United States Patent [19]

McFarlane et al.

[11] Patent Number: 5,164,405

[45] Date of Patent: Nov. 17, 1992

[54] NICARDIPINE PHARMACEUTICAL COMPOSITION FOR PARENTERAL ADMINISTRATION

[75] Inventors: Calum B. McFarlane, Linlithgow; Alistair B. Selkirk, Edinburgh; Michael J. Dey, East Calder, all of Scotland

[73] Assignee: Syntex (U.S.A.) Inc., Palo Alto, Calif.

[21] Appl. No.: 600,277

[22] Filed: Oct. 22, 1990

Related U.S. Application Data

[63] Continuation-in-part of Ser. No. 317,171, Feb. 28, 1989, abandoned.

[51] Int. Cl.$^5$ .............................................. A61K 31/44
[52] U.S. Cl. .................................................... 514/354
[58] Field of Search ........................................ 514/354

[56] References Cited

U.S. PATENT DOCUMENTS 3,985,758  10/1976  Murakami et al. ........... 260/295.5 R
4,711,902  12/1987  Serno ................................... 514/356

FOREIGN PATENT DOCUMENTS 0162705  11/1985  European Pat. Off. .
0200068   5/1986  European Pat. Off. .
3316510   8/1984  Fed. Rep. of Germany .
3339861   5/1985  Fed. Rep. of Germany .

*Primary Examiner*—S. J. Friedman
*Attorney, Agent, or Firm*—David A. Lowin; Tom M. Moran

[57] ABSTRACT

There is disclosed a stable pharmaceutical composition containing nicardipine hydrochloride, a non-chloride isotonicity agent, a buffering agent and a pharmaceutically acceptable aqueous vehicle for parenteral administration.

9 Claims, 2 Drawing Sheets

NICARDIPINE PHARMACEUTICAL COMPOSITION FOR PARENTERAL ADMINISTRATION

This is a continuation of pending application Ser. No. 07/317,171 filed Feb. 28, 1989, now abandoned incorporated herein by reference.

BACKGROUND OF THE INVENTION

1. Field of the Invention

This invention relates to an aqueous pharmaceutical composition containing nicardipine hydrochloride in a therapeutically effective amount suitable for parenteral administration, especially intraveneous administration.

2. Description of Related References

Nicardipine is a member of the class of drugs referred to as calcium channel blocking agents (also referred to as calcium entry blocking agents).

The chemical name for nicardipine, which is used primarily as its hydrochloride salt, is as follows:
2-(Benzylmethylamino)ethyl methyl 1,4-dihydro-2, 6-dimethyl-4-(m-nitrophenyl)-3,5-pyridine-dicarboxylate monohydrochloride.

Nicardipine hydrochloride, its preparation, and its use are described in U.S. Pat. No. 3,985,758 (Oct. 12, 1976).

GENERAL BACKGROUND

Administration of a drug by injecting a pharmaceutical composition containing such drug—parenteral administration—affords a number of advantages including, but not necessarily limited to, the following:

(1) An almost immediate response may be obtained by administering by intravenous injection a solution, usually aqueous, of the drug;

(2) The therapeutic response by a patient to a drug may be more readily controlled by administering the drug parenterally; and (3) A drug can be administered parenterally to a patient when it cannot be administered orally because of the unconscious or uncooperative state of the patient, or because of inactivation or lack of absorption in the intestinal tract.

Since most liquid solutions for injection are quite dilute, the component present in the highest proportion in a pharmaceutical composition is the pharmaceutically acceptable carrier (also referred to as the vehicle). The vehicle normally should have minimal pharmacological activity and toxicity but, still the vehicle is of great importance in the formulation since it presents the active constituent for absorption and/or distribution by the body fluids and tissues.

Aqueous vehicles for solutions are normally the least pharmacologically active and the least toxic over a wide volume range. They are therefore the primary vehicles of choice. Modification of the aqueous vehicle by displacing a minor proportion (49% or less of total of the aqueous vehicle) with a pharmaceutically acceptable nonaqueous water-miscible solvent can alter absorption and distribution patterns and normally results in a vehicle with more potential, pharmacological properties, and toxicity in its own right. A number of such solvents that are miscible with water have been used as a portion of the vehicle in the formulation of parenterals. These solvents are used primarily to effect solubility of certain drugs and to improve stability. The most important solvents in this group are ethyl alcohol, polyethylene glycol, and propylene glycol. Such preparations are usually administered intramuscularly. The most important group of nonaqueous vehicles are the fixed oils which must be of vegetable origin in order that they may be metabolized, must be liquid at room temperature, and must not become rancid rapidly. They are rarely used in intravenous preparations.

There has been observed the occurrence of visible as well as invisible physical, chemical and therapeutic incompatibilities when certain drugs or vehicle components are combined or added to injectable pharmaceutical compositions or intravenous fluids. Development of a precipitate or a color change in an injectable composition is a warning that an alteration has occurred. Such a composition should not be administered to a patient since in the former case the solid particles may occlude the blood vessels, the therapeutic agent may not be available for absorption and/or distribution or in the latter case the drug may have degraded into undesirable substances. These incompatibilites in the composition may arise due to effects of pH, ionic concentrations or chemical reactions. Losses in potency of a drug with infusion fluids may also occur due to adsorption onto infusion containers or devices.

In formulating a nicardipine solution for injection, a salt of nicardipine is preferred, especially nicardipine hydrochloride, as the salts generally are more water soluble and do not require the use of solubilizing agents. We have found, however, that dissolving of nicardipine hydrochloride in water for injection, as is described in the above-mentioned U.S. Pat. No. 3,985,758, is limited by nicardipine hydrochloride solubility in an aqueous solution and is accompanied by the formation of nicardipine free base which precipitates from solution and forms a yellow sticky substance adhering to the stirring system. Prolonged stirring is necessary for its removal. Thus, there is a need to formulate a stable aqueous pharmaceutical composition of nicardipine hydrochloride, suitable for parenteral administration or administration by infusion, which may be diluted in additional water or a mixture of water and water-miscible fluids.

SUMMARY OF THE INVENTION

This invention is a pharmaceutical composition suitable for parenteral administration to mammals and useful in the treatment of disease conditions that may be alleviated by the administration of calcium channel blocking agents, including cardiovascular and cerebrovascular disease conditions, comprising:

(a) a therapeutically effective amount of nicardipine hydrochloride;

(b) a physiologically and pharmaceutically acceptable non-chloride compound effective to render the pharmaceutical composition isotonic;

(c) a physiologically and pharmaceutically acceptable buffer in an amount effective to maintain the pH of the composition at about 3.0 to about 4.5; and (d) a pharmaceutically acceptable aqueous vehicle comprising at least a major proportion of water.

In another aspect, this invention is in a process for producing a stable pharmaceutical composition containing nicardipine hydrochloride suitable for parenteral administration and useful in the treatment of disease conditions which may be alleviated by the administration of calcium channel blocking agents, including cardiovascular and cerebrovascular disease conditions, comprising admixing a therapeutically effective amount of nicardipine hydrochloride and a pharmaceutically acceptable aqueous vehicle comprising at least a major proportion of water, the improvement comprising further admixing (a) a physiologically and pharmaceutically acceptable non-chloride compound effective to render the pharmaceutical composition isotonic and (b) a physiologically and pharmaceutically acceptable buffer in an amount effective to maintain the pH of the pharmaceutical composition at about 3.0 to about 4.5.

DETAILED DESCRIPTION OF INVENTION

The "active ingredient" component in the pharmaceutical composition according to this invention is nicardipine hydrochloride.

As is described above, nicardipine and its pharmaceutically acceptable salts and the preparation and use thereof is known as is disclosed in U.S. Pat. No. 3,985,758.

Nicardipine hydrochloride is present in a "therapeutically effective amount." By "therapeutically effective amount" as applied to nicardipine hydrochloride is meant that amount which when administered to mammals, especially human patients but also, for example, cattle, sheep and horses, will have a calcium entry blocking effect that will be useful to treat their disease conditions, that is, conditions which may be alleviated by the administration of calcium channel blocking agents, especially cardiovascular and cerebrovascular disease conditions. By the expression "disease conditions which may be alleviated by the administration of calcium channel blocking agents" is meant those pathological conditions which may be corrected, either therapeutically or prophylactically, by the use of the class of compounds known in the pertinent art as "calcium channel blocking agents." The therapeutically effective amount of the active ingredient nicardipine hydrochloride, in the aqueous vehicle broadly, i.e preferably, may range from about 0.5 mg/ml to about 10 mg/ml, more preferably from about 1 mg/ml to about 5 mg/ml, most preferably about 1 mg/ml to about 2.5 mg/ml based on amount of aqueous vehicle. The dose of active ingredient may range from about 0.01 to about 10 mg/kg of body weight based on a 70 kg patient.

Figure 1:
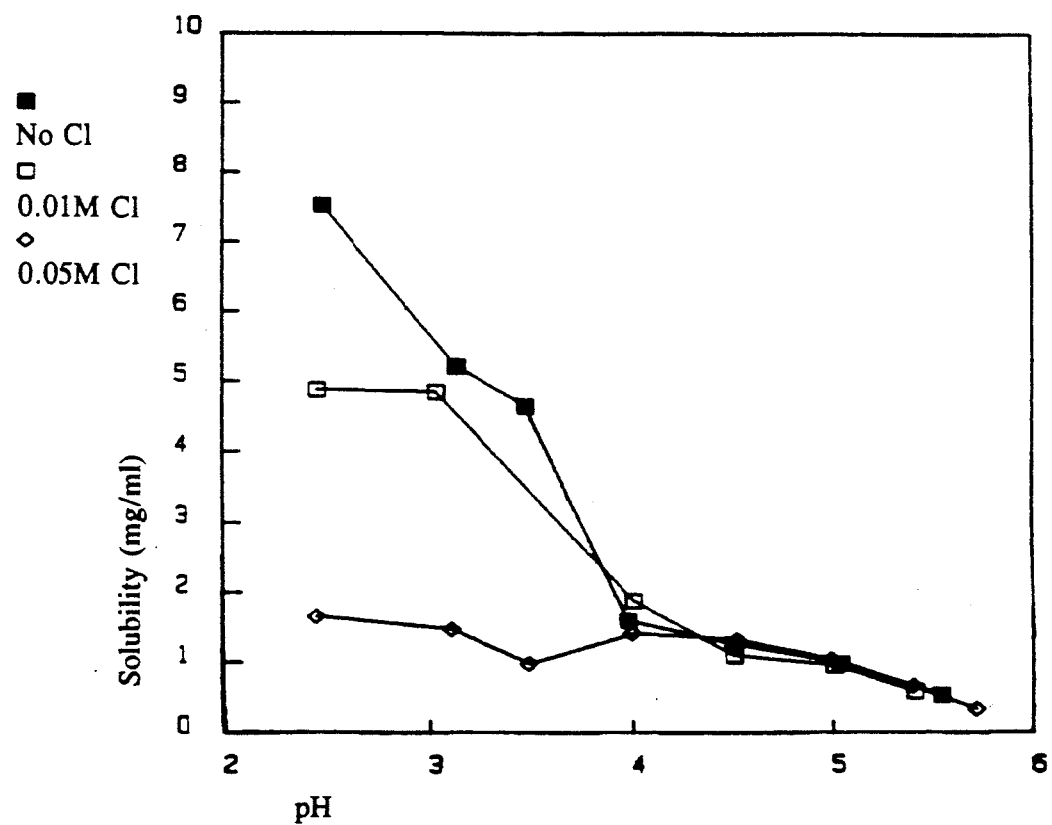
FIG. 1 illustrates the effect of added chloride ion on the solubility of nicardipine hydrochloride at various pH.

The physiologically and pharmaceutically acceptable non-chloride compound used to render the pharmaceutical composition isotonic preferrably may be selected from monohydric and polyhydric compounds. The term "isotonic" is used in its conventional sense, as is described in "Remington's Pharmaceutical Sciences," Mack Publishing Company, Easton, Pa., 1985, Chapter 80, page 1455 et seq., especially page 1456, left column, lines 24–33, to mean a fluid corresponding to body fluids including blood and lacrimal fluid, normally having an osmotic pressure which is often described as corresponding to that of a 0.9% solution of sodium chloride. More preferably the non-chloride compound may be selected from the group of polyhydric compounds comprising saccharides and non-saccharide polyhydric compounds. Suitable saccharides include sorbitol, mannitol, dextrose and glucose. Suitable polyhydric compounds which are non-sugar compounds include polyethylene glycol (PEG) and glycerol. When glycerol issued, care must be taken to avoid haemolysis. Most preferably, the non-chloride compound, used as an compound is a saccharide compound. Especially preferred as the non-chloride compound, used as an isotonicity agent, is sorbitol in the amount of about 48 mg/ml to about 50 mg/ml of aqueous vehicle. The non-chloride compounds are important because their use avoids precipitation of nicardipine. Although the precise cause for such precipitation of nicardipine is not fully understood, one explanation may be the following: As shown in FIG. 1, the use of chloride containing compounds restricts the solubility of nicardipine hydrochloride thus limiting the dose strengths available for the parenteral dose form. This reduction in solubility may be attributed to a common ion effect between the nicardipine hydrochloride and the chloride ions of the vehicle, inhibiting ionization of the nicardipine hydrochloride and thereby reducing its solubility. This effect is well described in many standard textbooks of physical chemistry such as "Physical Pharmacy", Lea and Febiger Publishing Company, Philadelphia, 1970, Chapter 10, pages 237–238.

The control of pH of the formulation is also essential to maintain the aqueous solubility of the nicardipine salts to a sufficient extent that the therapeutically desirable dose strengths can be manufactured and are physically stable, i.e. do not give evidence of precipitation. Maintenance of the necessary pH range can be best controlled by the use of a suitable buffer system.

The pharmaceutically acceptable buffer may be selected from any of the buffers that are effective to maintain the pH in the range of about 3.0–4.5, which buffers are well-known in the art to which this invention relates. More preferably, the buffer may be selected from citrate, acetate, phosphate and lactate buffers. Most preferably, the buffer is a citrate or acetate buffer, for example, citric acid plus sodium hydroxide in appropriate proportions which will maintain the pH at about 3.5–4.5. Use of citrate buffer in an amount sufficient to maintain a concentration in the range of 0.002M to 0.003M has been found to afford advantages in maintaining the pH of the composition in the range of about 3.5–4.5.

Referring to the citrate buffer (citrate buffer system) by way of example, i.e. the buffer is essentially a mixture of a sodium citrate prepared by the neutralization of, citric acid by sodium hydroxide plus residual citric acid. The ratio of citric acid to sodium citrate determines the pH of the buffer. Such a buffer system is well known to those skilled in the art and is described in neary all standard textbooks e.g., Physical Pharmacy by A. N. Martin, J. Swarbrick and A. Cammarata, Lee and Fabiger, 2nd edition, page 237 onwards.

The buffer system is useful over the desired dose range of the composition to provide ease of manufacture of the composition, to maintain pH stability during and after manufacture including terminal sterilization by autoclaves and thus to render the composition compatible with a range of infusion fluids.

Although the pharmaceutically acceptable carrier in the pharmaceutical composition may be selected from 100% of water (water for injection) or an aqueous system (that is an aqueous vehicle) comprising at least a major proportion of water, preferably the vehicle is water alone, without any co-solvent. By "major proportion" is meant at least 51% of the aqueous vehicle is water and the balance comprising one or more pharmaceutically acceptable non-aqueous, water-miscible cosolvents, such as ethanol and glycols.

With regard to the process for producing the stable pharmaceutical composition according to the inventions, preferably the citric acid and sodium hydroxide is first dissolved in some water for injection to form a solution of the desired pH. The nicardipine HCl and sorbitol are then added and dissolved in this solution of controlled pH and the resulting solution made to volume with the remainder of the water for injection. The important step is to dissolve the nicardipine HCl in the buffer solution to maintain the pH of the liquid into which the Nicardipine HCl is dissolving to avoid formation of the free base of nicardipine with its resultant sticking and very slow dissolution. If the Nicardipine HCl and sorbitol are dissolved in the buffer solution no particular temperature or stirring conditions are required, i.e. if dissolved in buffer the process is very easy; if dissolved in water, i.e. either before buffer addition or in the unbuffered formulation process it is difficult and can require elevated temperatures, e.g. to 60-70° C. and prolonged mixing.

The following examples and tables are illustrative of the invention and are not to be construed as limiting the scope of the invention.

EXAMPLE I

Effect of Added Chloride Ion on Solubility of Nicardipine Hydrochloride

In this example, there was demonstrated, as set forth in FIG. 1, the aqueous solubility of nicardipine hydrochloride as a function of pH and in the presence of a range of chloride concentrations in the dissolution medium. The solubilities were equilibrium solubilities measured by a saturated solution method well known to those skilled in the art.

The results indicated a reduction in the aqueous solubility as the pH increases and as the chloride ion concentration increases.

EXAMPLE II

Nicardipine Hydrochloride Formulations

In this example, a variety of nicardipine hydrochloride formulations and pharmaceutical compositions were prepared in an effort to obtain a stable pharmaceutical composition containing 1 mg of nicardipine hydrochloride per ml.

A. In an initial attempt to formulate a pharmaceutical composition of nicardipine hydrochloride suitable for parenteral administration employing conventional techniques well known in the pertinent art, 1 mg of nicardipine hydrochloride was dissolved in water for injection. To this was admixed 6 mg of sodium chloride and a sufficient amount of hydrochloric acid to give a solution having a pH of 3 5. This solution was then made up to volume with water for injection, i.e., to 1 ml. The resulting composition was packaged in an ampule and sterilized by autoclaving. This composition is set out in Table 1 as Example A. The 6 mg of sodium chloride was the maximum amount of sodium chloride which could be added to the composition while achieving the desired nicardipine concentration. This amount of sodium chloride results in a hypotonic solution which is far less pharmaceutically desirable. Increasing the amount of sodium chloride to a level necessary to give an isotonic solution results in failure to dissolve sufficient nicardipine hydrochloride to manufacture the required dose strength of 1 mg per ml. This is ascribed to the common ion effect previously described. Accordingly the formulation set out in Example A of Table 1 was unsatisfactory.

B. Then, in a following attempt to formulate a pharmaceutical composition of nicardipine hydrochloride for parenteral administration employing conventional techniques well known in the pertinent art, 1 mg of nicardipine hydrochloride together with about 50 mg of the non-chloride, saccharide compound, sorbitol, were dissolved in a portion of water for injection. Sufficient amounts of concentrated hydrochloric acid was added to produce a solution of pH 3.5 and the composition was made to volume with the remainder of the water for injection, i.e. to 1 ml. The resulting composition was packaged in an ampule and sterilized by autoclaving. This composition is set out in Table 1 as Example B.

The use of sorbitol in amounts to maintain isotonicity appeared to produce a stable isotonic solution suitable for parenteral use. However, it was found that upon autoclaving, the pH of the sorbitol formulation, and also the sodium chloride formulation of Example A, were subject to pH change in glass ampules from several different suppliers. See Table 3. In addition considerable difficulties were found in the manufacture of the formulations, given in Examples A and B, due to the precipitation of nicardipine free base when the nicardipine hydrochloride was dissolved in the water for injection prior to pH adjustment with concentrated hydrochloric acid. We have found that the precipitation is due to a lack of pH control at this stage which allowed the pH to rise as the nicardipine hydrochloride is dissolved until the free base precipitates. This precipitation necessitates very prolonged mixing times to completely dissolve the nicardipine and increases the potential for the manufacture of sub-potent batches if these prolonged mixing times do not result in complete dissolution of the nicardipine. The formulation set out in Example B was also unsatisfactory.

C. In order to overcome both the manufacturing problems and the pH changes, it was conceived to add a dilute buffer solution to the sorbitol formulation of Example B.

More specifically, in accordance with the formulation set out as Example 1, Table 2, 1 mg of nicardipine hydrochloride and 48.9 mg of sorbitol were dissolved in a solution of 0.525 mg of citric acid and 0.09 mg of sodium hydroxide in a portion of the water for injection. The solution was made up to volume, i.e 1 ml. with the remainder of the water for injection. This solution was then filled into ampules and terminally sterilized by autoclaving. A similar procedure was adopted for Example 2 in Table 2 except 2.5 mg of nicardipine hydrochloride was dissolved instead of 1 mg and a corresponding lower amount of sorbitol, 48.0 mg, was also dissolved to achieve isotonicity. Upon subjection to autoclaving, the compositions according to Examples 1 and 2 remained stable. Thus has been provided and produced a stable isotonic solution containing nicardipine hydrochloride which is suitable for parenteral use and which is not affected by the sterilization procedure (Table 2, composition of Example 1). The amount of buffer, namely citric acid monohydrate and sodium hydroxide added (0.0025M citrate equivalent) was sufficient to maintain the pH in the range of 3.5 to 3.8 after autoclaving (Table 3) but was sufficiently dilute to be buffered by body fluids on injection. No detrimental effect on product stability with respect to pH was introduced by the addition of citrate buffer over the range 0.002-0.003M (Table 4). The addition of the sorbitol and nicardipine hydrochloride to the buffer solution resulted in rapid and complete dissolution of both materials. No precipitation of free base was observed, analysis of the solutions confirmed their potency and no prolonged mixing times were necessary.

From solubility data (Table 5), alternative buffer concentrations were evaluated. A solution containing 2.5 mg of nicardipine HCl per ml of solution was prepared (Table 2, composition of Example 2). Stability studies indicate results substantially identical to the results obtained with the composition of Example 1 which contains nicardipine HCl in the amount of 1 mg/ml solution. Filtration of the solutions through a 0.22 micron filter was accomplished easily regardless of the formulation or concentration. The aqueous solutions readily passed through the filters used (Millipore GSWP or Durapore) with no apparent problems. Terminal sterilization by autoclaving was used to insure product sterility.

The use of various excipient limits did not appear to affect product quality or stability. Varying the citrate buffer content from 0.002 to 0.003M citrate did not affect the product quality. No significant changes in pH or potency were evident on autoclaving (Table 6). Stability data shows excellent stability for up to 3 years at 25° C., with no significant loss in potency or change in solution pH (Table 7).

TABLE 1

Unsatisfactory Prior Art Formulations of Nicardipine HCl (1 mg/ml) for Injection

|  | Example A | Example B |
|---|---|---|
| Nicardipine HCL | 1.0 mg | 1.0 mg |
| Sodium Chloride | 6.0 | 0 |
| Sorbitol | 0 | 50.0 mg |
| Hydrochloric acid | qs to pH 3.5 | qs to pH 3.5 |
| Water for Injection | qs to 1.0 ml | to 1.0 ml |

TABLE 3 pH Changes Induced by Autoclaving for Various Nicardipine Injection 1 mg/ml formulations

| Sample Composition | Ampule | Initial pH (before) | Final pH (after) |
|---|---|---|---|
| Sodium Chloride Formula (Ex. A) | A | 3.60 | 4.82 |
| Sorbitol Formula (Ex. B) | A | 3.55 | 4.33 |
|  | B | 3.55 | 4.20 |
| Buffered Sorbitol (0.0025M citrate) (Ex. 1) | A | 3.51 | 3.65 |
|  | B | 3.51 | 3.60 |

Ampuls:
A = FBG Trident; 5 ml Type 1 amber glass
B = Epsom Glass; 5 ml Type 1 amber glass

TABLE 4

Nicardipine HCl Injection Composition
Effect of Buffer Strength
Citric Acid/Sodium Hydroxide amount altered: pH 3.5

| Buffer Strength (M) | pH at Manufacture | pH after Autoclaving | Nicardipine HCl Content % Label Strength |
|---|---|---|---|
| 0.002 | 3.54 | 3.83 | 102.7 |
| 0.0025 | 3.55 | 3.85 | 101.4 |
| 0.003 | 3.50 | 3.80 | 101.6 |

TABLE 5

Equilibrium Solubility Data for Nicardipine Hydrochloride

|  | pH | Solubility mg/ml |
|---|---|---|
| 4° C. | 3.05 | 2.94 |
|  | 3.45 | 3.28 |
|  | 4.06 | 2.95 |
| 25° C. | 4.06 | 5.16 |
|  | 4.24 | 2.35 |
|  | 4.68 | 0.85 |
|  | 5.05 | 0.36 |
|  | 6.21 | 0.025 |

TABLE 6

Nicardipine HCl Content of Buffered Sorbitol Injection Formulation After Various Sterilization Processes

| Sterilization cycle (°C./minute) | Nicardipine Content (% label) Mean ± s.d. | | pH (Mean ± s.d.) | |
|---|---|---|---|---|
|  | Before[1] | After[1] | Before | After |
| 115/30 | 101.4 ± 0.34 | 101.4 + 0.57 | 3.64 + 0.057 | 3.60 + 0.025 |
| 121/15 | 101.4 + 0.34 | 99.7 + 0.34 | 3.64 + 0.057 | 3.63 + 0.028 |
| 115/30 | 102.1 + 0.53 | 101.2 + 0.93 | 3.60 + 0.007 | 3.64 + 0.017 |
| 121/15 | 101.4 + 0.34 | 101.8 + 0.33 | 3.64 + 0.057 | 3.60 + 0.012 |
| 121/15 | 100.4 + 0.16 | 99.4 + 0.35 | 3.71 + 0.081 | 3.73 + 0.056 |

[1]No degradation products were observed using a stability indicating h.p.l.c. method.

TABLE 2

Nicardipine Hydrochloride Pharmaceutical Composition for Parenteral Administration

|  | Composition of Ex. 1 (1 mg/ml) | Composition of Ex. 2 (2.5 mg/ml) |
|---|---|---|
| Nicardipine HCl | 1.0 mg | 2.5 mg |
| Sorbitol BP | 48.9 mg | 48.0 mg |
| Sodium Hydroxide | 0.09 mg | 0.09 mg |
| Citric Acid Monohydrate BP | 0.525 mg | 0.525 mg |
| Water For Injection | qs ad 1.0 ml | qs ad 1.0 ml |

TABLE 7

Stability Data for Nicardipine HCL Injection Stored at 25° C.

| Time (Months) | Nicardipine HCl Content (% label) | PH | Appearance |
|---|---|---|---|
| Initial | 99.4 | 3.81 | Clear Pale Yellow Solution |
| 3 | 98.9 | 3.78 | No change |
| 6 | 99.2 | 4.01 | No change |
| 12 | 98.5 | 3.96 | No change |
| 18 | 96.7 | 4.02 | No change |
| 24 | 97.3 | 4.05 | No change |
| 36 | 97.0 | 3.90 | No change |

EXAMPLE III

Compatibility Testing with Infusion Fluids

Nicardipine hydrochloride solution for parenteral administration was diluted (1:10) in a range of infusion fluids used as received in 500 ml Viaflex ® containers from Bextex Healthcare. The solutions were thoroughly mixed and stored at room temperature. Samples were removed at intervals up to 24 hours for nicardipine hydrochloride determination using a stability indicating method. The pH and appearance were also observed and recorded.

No changes in appearance were noted and no degradation products observed in any sample.

No significant losses in potency occurred with the majority of fluids (Table 8), but a number of fluids showed a decrease in concentration over the test period indicating incompatibility. This loss, due to partition into and onto the PVC material occurred at pH greater than about pH 4.5, when the pH was measured immediately after mixing. The solution showing incompatability showed initial pH values in the region of pH 6–7 and this was insufficiently reduced by the presence of the dilute citrate buffer in the parenteral formulation. For other fluids showing compatability, those with pH values greater than 4–5 (before addition of the nicardipine hydrochloride solution for parental use), showed reductions in pH values to below pH 4.5 (after the addition of nicardipine hydrochloride solution for parenteral use), this being due to the presence of dilute buffer in the parenteral formulation. This effect is further illustrated in the next Example.

EXAMPLE IV

Improved Compatibility with Buffered Formula

Figure 2:
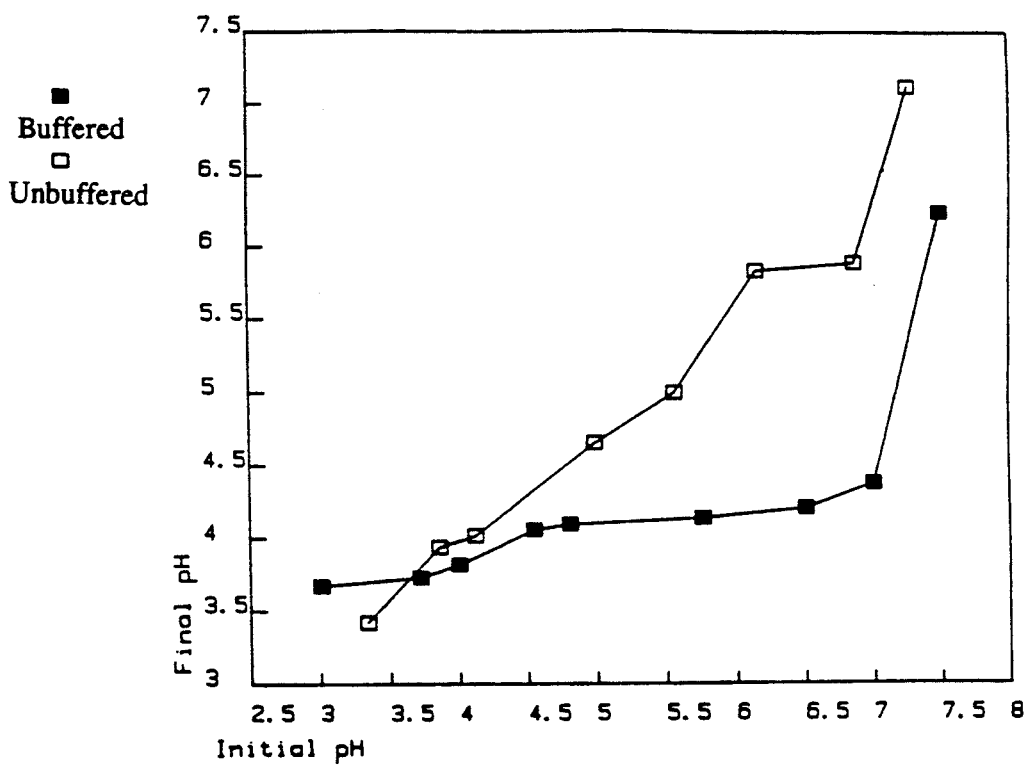
FIG. 2 illustrates the effect of initial pH of dextrose injection on the final pH after mixing with buffered and unbuffered injection solution.

Comparison of a buffered formula (0.0025M citrate equivalent) and unbuffered formula using Dextrose 5% Injection solution, of various pH from pH 3–7.5, using a 1:10 dilution, showed improved compatability for the buffered formula since the pH after mixing remained below pH 4.5 for Dextrose Injections solutions up to pH 7, in comparison to the unbuffered formula which showed pHs after mixing above pH 4.5 (Tables 9 and 10 and FIG. 2). The higher pH values after mixing were also associated with precipitation of nicardipine, thus being more prominent for the unbuffered formula.

TABLE 8

Summarized Compatibility for Nicardipine HCl Injection Diluted With Various Infusion Fluids

| COMPATIBLE WITH | INCOMPATIBLE WITH |
|---|---|
| Dextrose 5% | Compound Sodium Lactate |
| Sodium Chloride 0.9% | Half strength Sodium Lactate and Dextrose 5% |
| Sodium Chloride 0.9% and Dextrose 5% | Darrows Solution |
| Potassium Chloride 0.3% and Dextrose 5% | |
| Potassium Chloride 0.3%, Sodium Chloride 0.18% and Dextrose 4% | |
| Potassium Chloride 0.3% and Sodium Chloride 0.9% | |
| Laevulose 10% | |
| Laevulose 20% | |
| Ringers Solution | |

TABLE 9

Effect of Initial pH of Dextrose 5% Injection on the Final Solution pH after addition of Nicardipine HCl Injection (Buffered Formula) to 100 mg.l$^{-1}$

| INITIAL pH (Before Addition) | FINAL pH (After Addition) | APPEARANCE (After Mixing) |
|---|---|---|
| 3.01 | 3.67 | Clear pale yellow solution |
| 3.72 | 3.73 | Clear pale yellow solution |
| 4.00 | 3.82 | Clear pale yellow solution |
| 4.55 | 4.06 | Clear pale yellow solution |
| 4.81 | 4.10 | Clear pale yellow solution |
| 5.76 | 4.14 | Clear pale yellow solution |
| 6.50 | 4.21 | Clear pale yellow solution |
| 7.00 | 4.38 | Clear pale yellow solution |
| 7.49 | 6.24 | Cloudy pale yellow solution with precipitation |

Initial pH of Nicardipine HCl Injection = 3.86

TABLE 10

Effect of Initial pH of Dextrose 5% Injection on the Final Solution of Nicardipine HCl Injection (Unbuffered Formula) to 100 mg · l$^{-1}$

| INITIAL pH (Before Addition) | FINAL pH (After Addition) | APPEARANCE (After Mixing) |
|---|---|---|
| 3.34 | 3.42 | Clear pale yellow solution |
| 3.86 | 3.94 | Clear pale yellow solution |
| 4.12 | 4.02 | Clear pale yellow solution |
| 4.99 | 4.66 | Clear pale yellow solution |
| 5.56 | 5.00 | Clear pale yellow solution |
| 6.14 | 5.83 | Clear pale yellow solution |
| 6.86 | 5.89 | Cloudy pale yellow solution |
| 7.26 | 7.11 | Cloudy pale yellow solution |

What is claimed is:

1. In a process for producing a stable pharmaceutical composition containing nicardipine hydrochloride suitable for parenteral administration and useful in the treatment of disease conditions which may be alleviated by the administration of calcium channel blocking agents, which process comprises admixing a therapeutically effective amount of nicardipine hydrochloride and a pharmaceutically acceptable aqueous vehicle comprising at least a major proportion of water, the improvement comprising:

(a) dissolving in an aqueous vehicle consisting essentially of water a physiologically and pharmaceutically acceptable buffer in an amount effective to maintain the pH of the pharmaceutical composition at about 3.0 to about 4.5, thereby forming a buffered solution; and (b) adding to said buffered solution
        at least 1 mg/ml of said therapeutically effective amount of nicardipine hydrochloride, and
        a physiologically and pharmaceutically acceptable non-chloride compound selected from saccharides, including sorbitol, mannitol, dextrose and glucose, and non-saccharides, including polyethylene glycol and glycerol, in an amount effective to render the pharmaceutical composition isotonic.

2. The process of claim 1 further comprising the step of terminally sterilizing said pharmaceutical composition by autoclaving.

3. A pharmaceutical composition suitable for parenteral administration to mammals and useful in the treatment of disease conditions which may be alleviated by the administration of calcium channel blocking agents, which composition comprises:

(a) a physiologically and pharmaceutically acceptable non-chloride compound selected from saccharides, including sorbitol, mannitol, dextrose and glucose, and non-saccharides, including polyethylene glycol and glycerol, in an ammount effective to render the pharmaceutical composition isotonic;

(b) a physiologically and pharmaceutically acceptable buffer, selected from citrate, acetate, phosphate, and lactate buffers, in an amount effective to maintain the pH of the composition at about 3.0 to about 4.5;

(c) a pharmaceutically acceptable aqueous vehicle consisting essentially of water; and (d) at least about 1 mg/ml nicardipine hydrochloride in solution herein.

4. A composition according to claim 3 wherein the therapeutically effective amount of nicardipine hydrochloride is from about 0.5 mg/ml to about 10 mg/ml of aqueous vehicle and the aqueous vehicle is water (water for injection) alone.

5. A composition according to claim 3 wherein the buffer is selected from citrate and acetate buffers.

6. A composition according to claim 3 wherein:
(a) the therapeutically effective amount of nicardipine hydrochloride is from about 1 mg/ml to about 2.5 mg/ml of aqueous vehicle;
(b) the non-chloride compound is a saccharide selected from sorbitol and mannitol used in an amount of about 48.0 to about 50.0 mg per ml of aqueous vehicle.
(c) the buffer is citrate used in an amount of about 0.002–0.003M; and
(d) the aqueous vehicle is water alone.

7. A composition according to claim 6 wherein the non-chloride compound is sorbitol.

8. A pharmaceutical composition suitable for parenteral administration useful in the treatment of cardiovascular and cerebrovascular conditions comprising:
(a) about 1.0 mg/ml of composition of nicardipine hydrochloride;
(b) about 48–50 mg/ml of sorbitol;
(c) an amount of citric acid monohydrate and sodium hydroxide sufficient to render the composition about 0.002–0.003M in citric acid monohydrate and having a pH of about 3.5–4.5; and
(d) sufficient water to make up 1 ml volume.

9. A pharmaceutical composition suitable for parenteral administration useful in the treatment of cardiovascular and cerebrovascular conditions comprising:
(a) about 2.5 mg/ml of composition of nicardipine HCl;
(b) about 48–50 mg/ml of composition of sorbitol;
(c) an amount of citric acid monohydrate sufficient to render the composition about 0.002–0.003M in citric acid monohydrate and having a pH of about 3.5–4.5; and
(d) sufficient water to make up 1 ml volume.

* * * * *

UNITED STATES PATENT AND TRADEMARK OFFICE
CERTIFICATE OF CORRECTION

PATENT NO. : 5,164,405

DATED : November 17, 1992

INVENTOR(S) : Mcfarlane, et al.

It is certified that error appears in the above-identified patent and that said Letters Patent is hereby corrected as shown below:

Claim 9, at column 12, line 25 "(c) an amount of citric acid monohydrate sufficient to" should read --(c) an amount of citric acid monohydrate and sodium hydroxide sufficient to--.

Signed and Sealed this

Twenty-sixth Day of October, 1993

*Attest:*

BRUCE LEHMAN

*Attesting Officer*  *Commissioner of Patents and Trademarks*